(12) United States Patent
Kim

(10) Patent No.: US 12,329,492 B2
(45) Date of Patent: Jun. 17, 2025

(54) TEST DEVICE FOR BODY FLUID ANALYSIS

(71) Applicant: INTIN CO., LTD., Daegu-si (KR)

(72) Inventor: Ji Hoon Kim, Seoul (KR)

( * ) Notice: Subject to any disclaimer, the term of this patent is extended or adjusted under 35 U.S.C. 154(b) by 755 days.

(21) Appl. No.: 17/054,180

(22) PCT Filed: Mar. 4, 2019

(86) PCT No.: PCT/KR2019/002460
§ 371 (c)(1),
(2) Date: Nov. 10, 2020

(87) PCT Pub. No.: WO2020/045778
PCT Pub. Date: Mar. 5, 2020

(65) Prior Publication Data
US 2021/0186333 A1  Jun. 24, 2021

(30) Foreign Application Priority Data
Aug. 28, 2018  (KR) ........................ 10-2018-0101355

(51) Int. Cl.
*A61B 5/00* (2006.01)
*A61B 10/00* (2006.01)
(Continued)

(52) U.S. Cl.
CPC ........ *A61B 5/0059* (2013.01); *A61B 10/0045* (2013.01); *A61B 10/0051* (2013.01);
(Continued)

(58) Field of Classification Search
CPC .............. A61B 5/0059; A61B 10/0045; A61B 10/0051; A61B 10/0058; G01N 21/17;
(Continued)

(56) References Cited

U.S. PATENT DOCUMENTS 5,104,619 A * 4/1992 de Castro ............ G01N 33/528
422/422
2008/0255472 A1  10/2008 Kuo
(Continued)

FOREIGN PATENT DOCUMENTS

CN       1448716 A    10/2003
CN    101413941 A     4/2009
(Continued)

OTHER PUBLICATIONS

English Translation of Hoon (KR20170071275) (Year: 2017).*
(Continued)

*Primary Examiner* — Elizabeth A Robinson
*Assistant Examiner* — Jonathan E Lepage
(74) *Attorney, Agent, or Firm* — ANTONIO HA & U.S. PATENT, LLC

(57) ABSTRACT

The present invention relates to a test device for body fluid analysis. The device according to the present invention comprises: a first assembly having a magnifying lens for magnifying and observing a target body fluid; a second assembly configured to be assembled to the first assembly and having a lens transmission hole for condensing light; and an observation sheet for receiving the target body fluid between the first assembly and the second assembly, wherein the observation sheet includes a body portion disposed inside the first assembly and the second assembly, and a handle portion extending from the body portion. According to the present invention, by providing a test device for body fluid analysis that can be easily carried and conveniently used by a user, the user can directly perform a body fluid test at a desired place and time, and immediately confirm an analysis result of the body fluid through a user terminal.

12 Claims, 5 Drawing Sheets

(51) Int. Cl.
*G01N 21/17* (2006.01)
*G01N 33/487* (2006.01)

(52) U.S. Cl.
CPC ........... *G01N 21/17* (2013.01); *G01N 33/487* (2013.01); *G01N 2201/063* (2013.01)

(58) Field of Classification Search
CPC .................. G01N 21/01; G01N 33/487; B01L 2300/0825
See application file for complete search history.

(56) References Cited

U.S. PATENT DOCUMENTS

| | | | |
|---|---|---|---|
| 2013/0203627 A1* | 8/2013 | Moll | ................ G01N 21/7703 506/18 |
| 2016/0147057 A1 | 5/2016 | Nagayama | |
| 2016/0290916 A1 | 10/2016 | Shoshan et al. | |
| 2018/0051313 A1* | 2/2018 | Rajagopal | ................ C12M 1/12 |
| 2020/0057288 A1 | 2/2020 | Schulze | |

FOREIGN PATENT DOCUMENTS

| | | | | |
|---|---|---|---|---|
| CN | 102472703 A | | 5/2012 | |
| CN | 107044983 A | * | 8/2017 | ........... G01N 33/487 |
| CN | 107144568 A | | 9/2017 | |
| CN | 108366787 A | | 8/2018 | |
| JP | 2004-535576 A | | 11/2004 | |
| JP | 2017-161301 | | 9/2017 | |
| KR | 10-2004-0013003 | | 2/2004 | |
| KR | 10-2013-0012744 | | 2/2013 | |
| KR | 10-2014-0127766 | | 11/2014 | |
| KR | 10-1533107 | | 7/2015 | |
| KR | 10-2017-0071275 | | 6/2017 | |
| KR | 10-2018-0057307 | | 5/2018 | |
| KR | 10-2019-0008189 | | 1/2019 | |
| WO | 2017140854 A1 | | 8/2017 | |

OTHER PUBLICATIONS

English Translation of Irisawa (JP2017161301) (Year: 2017).*
English Specification of 2017140854A1.
English Abstract of 10-2017-0071275.
English Abstract of 2017-161301.
English Abstract of 10-2004-0013003.
English Abstract of 10-2014-0127766.
English Abstract of 10-2013-0012744.
English Specification of JP2004-535576A.
English Specification of 10-2019-0008189.
English Specification of 10-1533107.
English Specification of CN101413941A.
English Specification of CN102472703A.
English Specification of CN107144568A.
English Specification of CN108366787A.
English Specification of CN1448716A.
English Specification of 10-2018-0057307.

* cited by examiner

TEST DEVICE FOR BODY FLUID ANALYSIS

TECHNICAL FIELD

The present disclosure relates to a test device for a body fluid, and more particularly, to a test device for analyzing a body fluid allowing a user to directly test a body fluid without restriction of place or time and check an analysis result of the body fluid through a user terminal.

BACKGROUND ART

In general, people have to visit a specialized medical institution to check their health or physical condition. However, in order to visit a specialized medical institution for a check-up, it is necessary to break down a busy daily schedule and perform a complicated procedure, which may incur much time and high cost. For this reason, most people tend to live with decent discomfort and use specialized medical institutions only when encountering pain or discomfort to a degree that is difficult to bear. In order to alleviate such inconvenience, technologies have been developed to frequently check a physical condition using various high-tech equipment and transmit a corresponding result to specialized medical institutions through a network to check, but such technologies have rarely commercialized and used actually.

Rather, simple testing devices that have been used from the past has been steadily increasingly used, and in particular, utilization thereof in younger generations has further increased because of its convenient usage, low cost, and alleviation of discomfort in case of using specialized medical institutions.

Such a test device detects biochemical substances such as hormones released in specific situations using secretions or body fluids, such as saliva, urine, sweat, blood or sperm, discharged from the human body, which has advantages of relatively high accuracy and ease of use and is mainly used as a test means such as pregnancy diagnosis, diabetes diagnosis, or blood sugar check.

In recent years, as the marriage age increases and stress increases, sterility and infertility couples are increasing, and due to this, the use of a pregnancy test device is on the rise. Such a pregnancy diagnosis test device may only determine a pregnancy status and is not helpful for users suffering from sterility and infertility. Moreover, even such a pregnancy test device may only determine a woman's pregnancy, and matters such as a woman's possibility of pregnancy and a man's ability to fertilize may be limitedly verified at specialized medical institutions.

In particular, a sperm test to check man's fertilizing power requires a man to ejaculate a semen sample in a laboratory, which may make him feel ashamed shy, and if he collects a sperm sample at home, he may be requested to quickly bring it a laboratory, which may risk sperm death during transport

DISCLOSURE

Technical Problem

An aspect of the present disclosure provides a test device for body fluid analysis that the user may simply carry around and use conveniently, so that the user may directly perform a body fluid test at a desired place and time and immediately check an analysis result of a body fluid through a user terminal.

In addition, the present disclosure includes any other objects that may be achieved from the configuration of the present disclosure described later, in addition to the explicitly mentioned object.

Technical Solution

According to an aspect of the present disclosure, there is provided a test device for a body fluid analysis, including: a first assembly having a magnifying lens for magnifying and observing a target body fluid; a second assembly configured to be coupled to the first assembly and having a lens transmission hole for concentrating light; and an observation sheet for receiving the target body fluid between the first assembly and the second assembly, wherein the observation sheet includes a body part disposed inside the first assembly and the second assembly and a handle part extending from the body part.

The first assembly may include a first assembly body, a seating recess formed on an inner side of the first assembly body allowing the observation sheet to be seated therein, a through hole formed in the seating recess and penetrating the first assembly body, and at least one coupling recess formed on an upper surface of the first assembly body so as to be assembled with the second assembly.

The handle part may be disposed in an outer space of the first assembly and the second assembly.

The first assembly may further include a first communication hole connecting the seating recess and the external space.

The magnifying lens may be installed in the seating recess.

The first assembly may further include a first circumferential step formed along an outer edge of the first assembly body to guide assembly according to coupling with the second assembly.

The second assembly may further include a second assembly body and at least one coupling protrusion formed on a lower surface of the second assembly body so as to be coupled with the at least one coupling recess.

The second assembly may further include a second communication hole formed in the second assembly body so that the handle part of the observation sheet is disposed in an external space.

The lens transmission hole may penetrate from an upper side to a lower side of the second assembly body.

The second assembly may further include a second circumferential protrusion formed to be stepped along an outer edge of the second assembly body to guide assembly according to coupling with the first assembly.

The body part may include a body fluid input part formed to allow the target body fluid to be injected thereinto and a body fluid guide part configured to guide the target body fluid injected into the body fluid input part so as to be observed in a field of view of the magnifying lens.

The body fluid input part may include at least one body fluid guide recess formed in the body part to guide injection of the target body fluid.

The first assembly may be detachably attached to a camera of a user terminal.

Advantageous Effects

As described above, the test device for a body fluid analysis according to an embodiment of the present disclosure may be simply carried around and conveniently used by the user and easily detachably attached to a camera portion of a user terminal. Therefore, the user may directly perform a test at a desired place and time and immediately check an analysis result of a body fluid through a user terminal.

In addition, the test device for a body fluid analysis according to an embodiment of the present disclosure may be used by both women and men. That is, women may check their ovulation period to check a time with a high chance of pregnancy and men may check their sperm status, thereby increasing a likelihood of pregnancy.

In addition, in using the test device for a body fluid analysis in a user terminal, the test device for a body fluid analysis may be easily attached and may be uniformly attached around a camera.

In addition, since the handle part that may be gripped by the user is provided on the observation sheet accommodating the body fluid, contamination of the body fluid by the user may be prevented and the observation sheet may be easily seated inside the test device for a body fluid analysis and separated therefrom.

Meanwhile, the effects of the present disclosure are not limited to those described above and other effects that may be derived from the configuration of the present disclosure described later are included in the effects of the present disclosure.

BEST MODES

Figure 1:
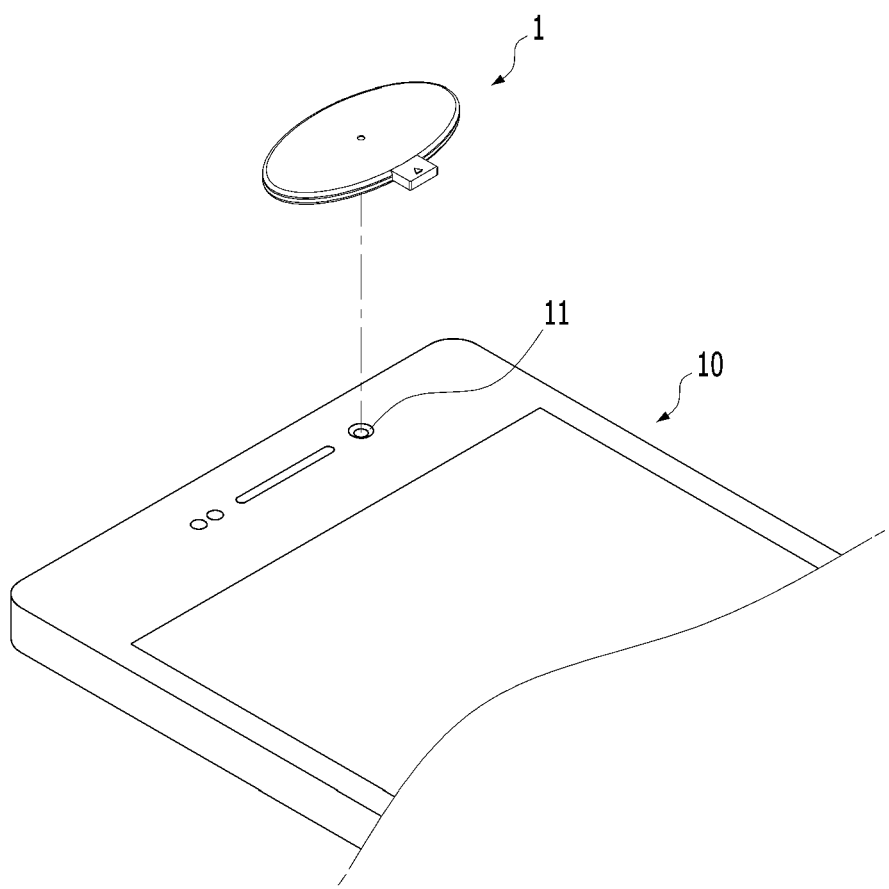
FIG. 1 is a view of a test device for a body fluid analysis mounted on a user terminal according to an embodiment of the present disclosure.

Terms or words used in the specification and claims should not be limited and construed as common or dictionary meanings, and should be construed as meanings and concepts according to the technical spirit of the present invention based on the principle that the inventor can appropriately define the concept of each term for describing the invention in the best way.

The embodiment described in the present disclosure and the configuration illustrated in the drawings are merely the most preferred embodiment of the present invention, rather than representing all the technical concepts of the present invention, so the present invention is meant to cover all modifications, similarities and alternatives which are included in the spirit and scope of the present invention at the time of filing of the present invention.

Figure 2:
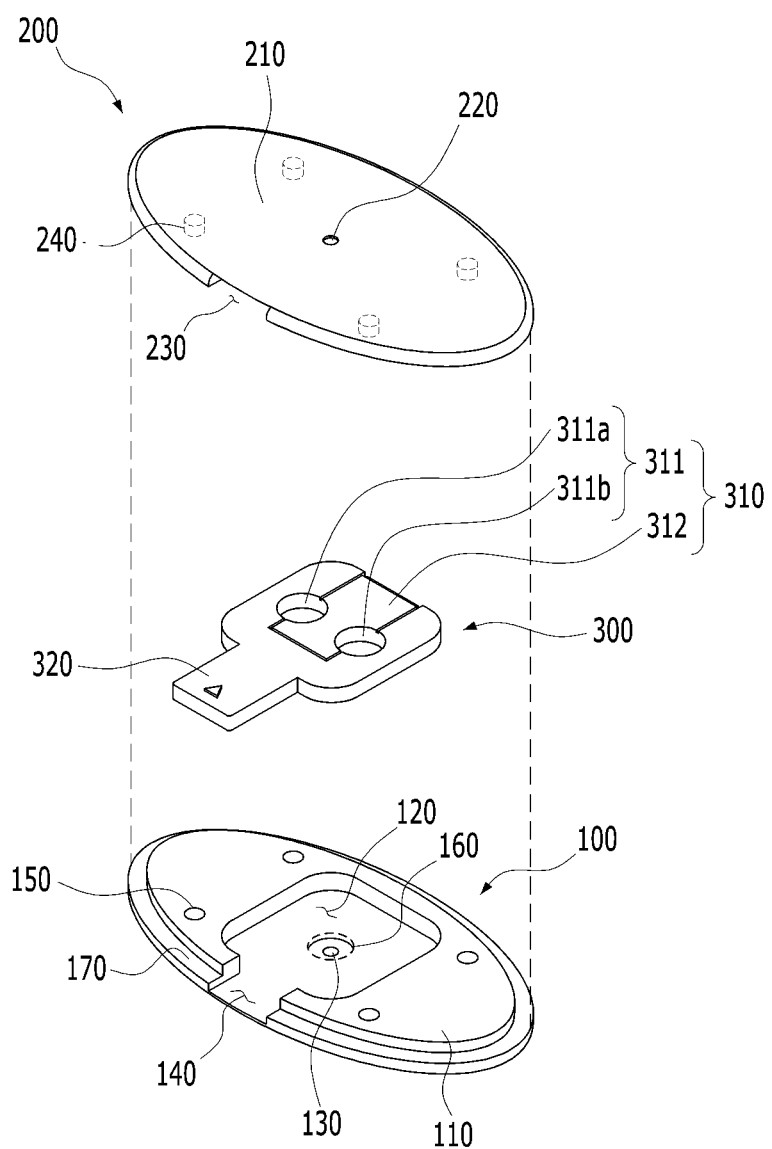
FIG. 2 is an exploded perspective view of a test device for a body fluid analysis according to an embodiment of the present disclosure.

FIG. 1 is a view of a test device for a body fluid analysis mounted on a user terminal according to an embodiment of the present disclosure and FIG. 2 is an exploded perspective view of a test device for a body fluid analysis according to an embodiment of the present disclosure.

As shown in FIGS. 1 and 2, a test device 1 for a body fluid analysis may image a target body fluid through a camera 11 of a user terminal 10 to generate a body fluid image, and a result of analyzing the body fluid image may be checked through the user terminal 10. The user terminal 10 may analyze the body fluid image through a pre-installed analysis program or analysis application and output the analyzed result so that the analyzed result may be provided to a user or may be transferred to a professional examination institution.

The test device 1 for a body fluid analysis includes a first assembly 100 detachably installed to the camera 11 of the user terminal 10, a second assembly 200 coupled to the first assembly 100, and an observation sheet 300 accommodating a target body fluid between the first assembly 100 and the second assembly 200.

The first assembly 100 is detachably installed to the camera 11 of the user terminal 10 and is configured so that the camera 11 may image the target body fluid. Here, the first assembly 100 may be attached to a portion near the camera 11 of the user terminal by an adhesive or may be selectively attached to or removed from the user terminal 10 through a separate mounting member formed in the form of a clip. Here, the mounting member is not limited to the clip form and may have any other various forms that may be attached to the user terminal 10.

Figure 3A:
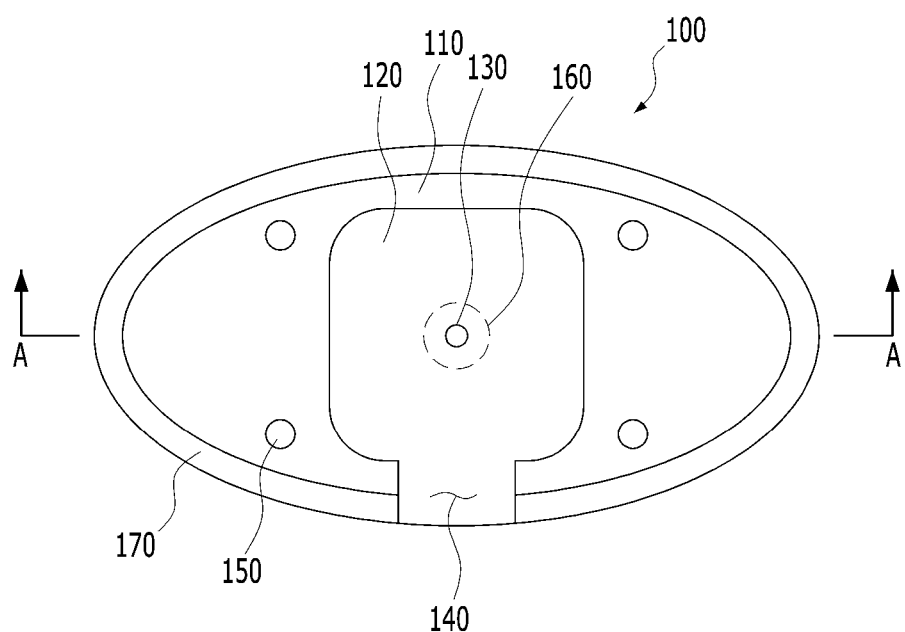
FIG. 3A is a plan view of a first assembly according to an embodiment of the present disclosure.
Figure 3B:
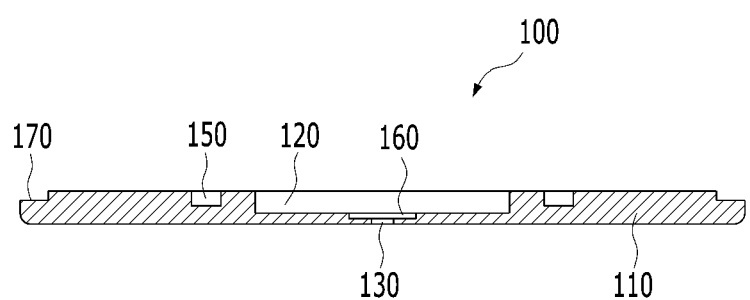
FIG. 3B is an enlarged cross-sectional view taken along line A-A shown in FIG. 3A.

FIG. 3A is a plan view of a first assembly according to an embodiment of the present disclosure and FIG. 3B is an enlarged cross-sectional view taken along line A-A of FIG. 3A.

Referring to FIGS. 3A and 3B, the first assembly 100 may include a first assembly body 110 as a flat plate, a seating recess formed to allow the observation sheet 300 to be seated on an inner side of the first assembly body 110, a through hole 130 formed in the seating recess 120 and penetrating the first assembly body 110, a first communication hole 140 connecting the seating recess 120 and the external space, and at least one coupling recess 150 formed on an upper surface of the first assembly body 110 so as to be assembled with the second assembly 200.

The first assembly body 110 may protect the target body fluid from an external shock or contamination and may be formed of a material which is strong against an external impact and light in weight, such as synthetic resin or a metal so that the camera 11 of the user terminal 10 may stably image the target body fluid. In addition, an outer surface of the first assembly body 110 may be colored with non-transmissive paint or formed of an opaque material so that light may be transmitted only in a limited portion. The seating recess 120 may be formed as a recess having a certain width at the center of an upper surface of the first assembly body 110. In particular, the seating recess 120 may be formed as a recess having a shape corresponding to the observation sheet 300, thereby stably supporting the observation sheet 300 and fixing the observation sheet 300 not to wobble, when the observation sheet 300 is seated therein. The through hole 130 is formed at the center of the seating recess 120 and penetrates the first assembly body 110. When attached to the user terminal 11, the test device 1 for a body fluid analysis may be located in a direction facing the camera 11 to image the target body fluid accommodated in the observation sheet 300 through the through hole 130. The first communication hole 140 may be formed to pass through an edge portion of the first assembly body 110 to connect the seating recess 120 and an external space. The first communication hole 140 may allow the handle part 320 of the observation sheet 300 to be described below to be seated therein and may have a shape corresponding to a cross section of the handle part 320. At least one coupling recess 150 may be formed on an upper surface of the first assembly body 110 and may be coupled with a coupling protrusion 240 of the second assembly 200 to be described below to assemble the first assembly 100 and the second assembly 200. For example, in case where two coupling recesses 150 are provided, the two coupling protrusions 240 may be provided on left and right sides of an upper surface of the first assembly body 110 and may be coupled with two coupling protrusions 240 provided at the second assembly 200, respectively.

In addition, the first assembly 100 may further include a magnifying lens 160 installed at the center of an inner side of the first assembly body 110, in particular, at the center of the seating recess 120 in which the observation sheet 300 is seated. When the target body fluid is observed through the magnifying lens 160, a pinhole effect may be obtained because the target body fluid may be magnified. Here, the pinhole effect is a phenomenon in which an object is visible relatively clearly when viewed through a small hole, and since light entering through the lens transmission hole 220 of the second assembly 200 to be described below enters in a straight line without having to be collected to one place, an exact image may be formed so that the target body fluid may be observed clearly. In this manner, the magnifying lens 160 compensates for an insufficient magnification ratio in the camera 11 of the user terminal 10 so that the target body fluid may be sufficiently magnified to be observed.

In addition, the first assembly 100 may further include a first circumferential step 170 formed to be stepped along an outer edge of the first assembly body 110 to guide assembly according to coupling with the second assembly 200. Accordingly, reinforcing may be provided in response to horizontal pushing when the first assembly 100 and the second assembly 200 may are assembled, and since positions of the first assembly 100 and the second assembly 200 according to coupling may be easily secured, assembling may be easily performed.

Figure 4A:
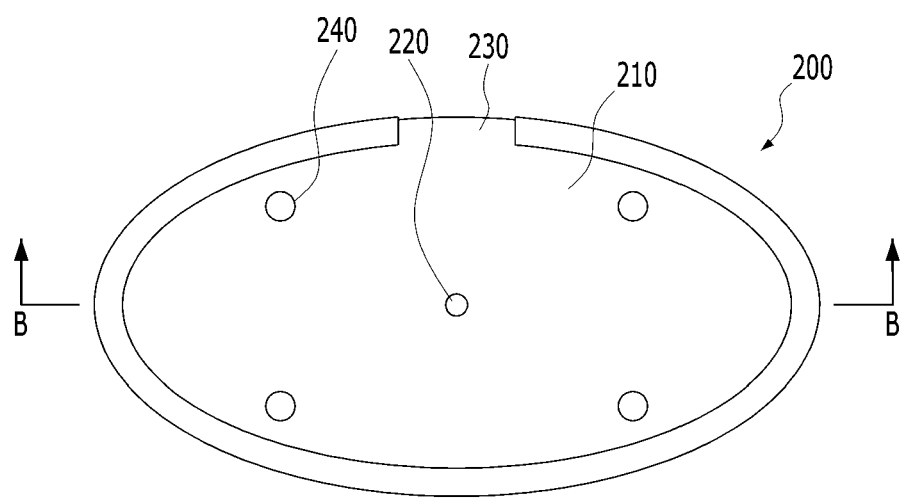
FIG. 4A is a plan view of a second assembly according to an embodiment of the present disclosure.
Figure 4B:
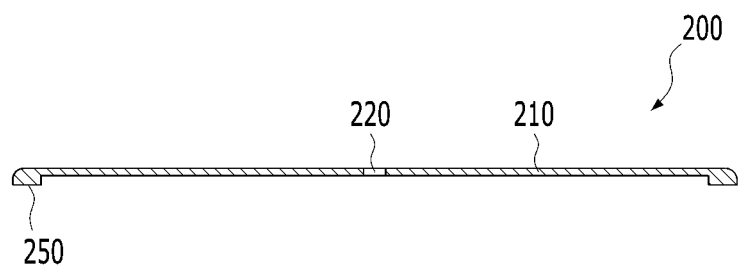
FIG. 4B is an enlarged cross-sectional view taken along line B-B shown in FIG. 4A.

FIG. 4A is a plan view of a second assembly according to an embodiment of the present disclosure, and FIG. 4B is an enlarged cross-sectional view taken along line B-B shown in FIG. 4A.

Referring to FIGS. 4A and 4B, the second assembly 200 may be configured to be assembled to an upper side of the first assembly 100 and may include a second assembly body 210 as a flat plate, a lens transmission hole 220 for concentrating light, a second communication hole 230 formed at the second assembly body 210, and at least one coupling protrusion 240 provided on a lower surface of the second assembly body 210 so as to be coupled with the coupling recess 150 of the first assembly 100.

The second assembly body 210 may protect the target body fluid from an external impact or contamination and may be formed of a material which is strong against an external impact and is light in weight such as a synthetic resin or a metal to stably image the target body fluid. In addition, an outer surface of the second assembly body 210 may be colored with non-transmissive paint or formed of an opaque material so that light may be transmitted only in a limited portion.

The lens transmission hole 220 may be a narrow vertical hole and may penetrate from an upper center of the second assembly body 210 to a lower side, and a periphery of the upper surface of the penetrated second assembly body 210 may be coated in black. Accordingly, more light may be absorbed to the narrow hole under the influence of black which absorbs light well.

The second communication hole 230 may be formed at a position corresponding to the first communication hole 140 and penetrates an edge portion of the second assembly body 210. That is, the second communication hole 230 may be formed in the second assembly body 210 so that the handle part 320 of the observation sheet 300 is disposed in an external space. Specifically, the second communication hole 230 may be configured to allow the handle part of the observation sheet 300 to be described below to be seated therein and may have a shape corresponding to a cross-section of the handle part 320. At least one coupling protrusion 240 may be formed to protrude from a lower surface of the second assembly body 210 and may be coupled to at least one coupling recess 150. That is, in case where two coupling protrusions 240 are provided, the two coupling protrusions 240 may be provided on left and right sides of a lower surface of the second assembly body 210 and installed at positions corresponding to the coupling recesses 150, so that the coupling protrusions 240 may be inserted into the coupling recesses 150, respectively, when the first assembly 100 and the second assembly 200 are coupled.

In addition, the second assembly 200 may further include a second circumferential protrusion 250 formed to be stepped along an outer edge of the second assembly body 210 to guide assembly according to coupling with the first assembly 100. Here, since the first circumferential step 170 installed on the edge of the first assembly 100 and the second circumferential protrusion 250 installed on the edge of the second assembly 200 may be installed to be coupled to correspond to each other, the first assembly 100 and the second assembly 200 may be easily assembled without adjusting a position according to the coupling of the first assembly 100 and the second assembly 200.

Figure 5:
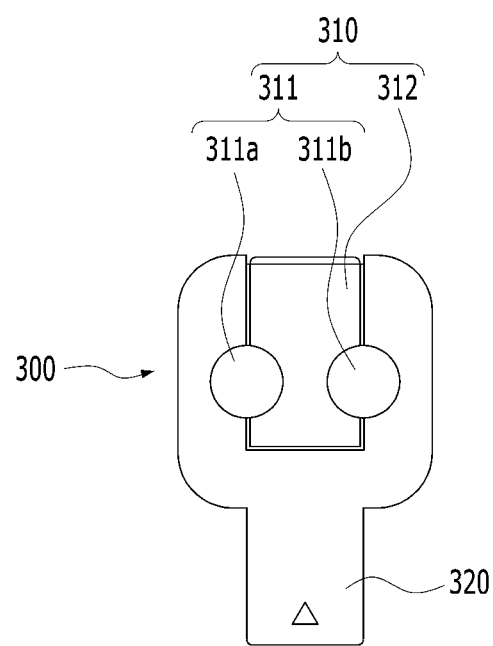
FIG. 5 is a plan view of an observation sheet according to an embodiment of the present disclosure

FIG. 5 is a plan view of an observation sheet according to an embodiment of the present disclosure.

Referring to FIG. 5, the observation sheet 300 serves as a stage which a target body fluid to be inspected is applied to and which allows the camera 11 of the user terminal 10 to image the target body fluid. To this end, the observation sheet 300 may include a body part 310 accommodating a target body fluid and a handle part 320 extending from the body part 310. The body part 310 may accommodate a certain amount of the target body fluid and may be formed as a thin plate. The body part 310 may be formed of a transparent material, such as a synthetic resin material including polycarbonate, polyethylene, or acrylic material or a glass material in order to allow light to be transmitted therethrough and to obtain a clear image. In addition, the body part 310 may be colored with a single color or a complementary color of the target body fluid so that the target body fluid may be clearly observed, or a film may be attached to one surface thereof.

The body part 310 may include a body fluid input part 311 allowing the target body fluid to be injected therein and a body fluid guide part 312 guiding the target body fluid injected into the body fluid input part 311 to be observed in the field of view of the magnifying lens 160. The body fluid input part 311 may include at least one body fluid guide recess 311a and 311b formed in the body part 310 to guide the input of the target body fluid. For example, the body fluid input part 311 may include a pair of body fluid guide recesses 311a and 311b respectively formed on left and right sides of the body part 310.

The body fluid guide part 312 may be inserted as a flat plate into the center of the body part 310 so that the target body fluid permeates an inner side of the center so as to be observed in the field of view of the magnifying lens 160, while protecting the target body fluid injected into the body fluid inlet 311. In addition, the body fluid guide part 312 may be formed higher than a bottom of the body fluid input part 311 and maintain a certain distance from the lens transmission hole 220 of the second assembly 200. When the target body fluid is dropped into the pair of body fluid guide recesses 311a and 311b, the target body fluid may permeate the inner side of the center of the body fluid guide part 312 from the body fluid guide recesses 311a and 311b. Here, an upper surface of the body fluid guide part 312, which is as a surface capable of absorbing a liquid, may be formed of a material such as paper or a porous synthetic resin, so that a predetermined amount of the target body fluid may be absorbed thereto.

The handle part 320 may extend from the body part 310 and may be disposed at an outer space of the first assembly 100 and the second assembly 200. The handle part 320 may be configured to be gripped by a user to easily insert the body part 310 into or remove the body part 310 from the seating recess 120 of the first assembly 100. Here, the handle part 320 may be formed of the same material as the body part 310, but is not limited thereto. In this manner, by implementing the handle part 320 on the observation sheet 300, the target body fluid may be prevented from being contaminated by the user and the observation sheet 300 is easily seated inside the test device 1 for a body fluid analysis or separated therefrom.

In addition, a direction indicator may be provided on the handle part 320 so that the user may easily check an input direction of the observation sheet 300.

Meanwhile, the handle part 320 may be disposed in an internal space of the first assembly 100 and the second assembly 200. That is, when the seating recess 120 is formed to have the same shape as a plane of the observation sheet 300, the handle part 320 may be seated inside the first assembly 100 and the second assembly 200 together with the body part 310. In this manner, when the body part 310 and the handle part 320 are disposed at the internal space of the first assembly 100 and the second assembly 200, the first assembly 100 and the second assembly 200 may not have the first communication hole 140 and the second communication hole 230.

Meanwhile, the first assembly 100 may be installed so that the through hole 130 is located in a direction facing the camera 11 of the user terminal 10 and light is controlled to be concentrated through the lens transmission hole 220 of the second assembly 200, whereby the target body fluid accommodated in the observation sheet 300 may be clearly observed through the magnifying lens 160.

That is, since light is concentrated through the lens transmission hole 220, clarity and brightness of the target body fluid observed in the observation sheet 300 may be increased with light that enters the magnifying lens 160, and thus a clear image may be displayed on the user terminal 10.

Hereinafter, a process of testing a target body fluid using the test device for a body fluid analysis according to an embodiment of the present disclosure will be described by way of example.

First, the first assembly 100 of the test device 1 for a body fluid analysis is mounted or attached to an upper side of the camera 11 of the user terminal 10, and the observation sheet 300 is subsequently seated in the seating recess 120 of the first assembly 100.

Next, a target body fluid may be dropped onto the body fluid input part 311 of the observation sheet 300 seated in the first assembly 100, and the second assembly 200 is subsequently coupled to an upper side of the first assembly 100, thereby finishing assembling. Alternatively, the observation sheet 300 in which the target body fluid is accommodated may be first seated in the seating recess 120 of the first assembly 100, the first assembly 100 in which the observation sheet is seated and the second assembly 200 may be coupled to be assembled, and thereafter, the test device for a body fluid analysis to which the first assembly 100 and the second assembly 200 may be mounted on or attached to the user terminal 10.

Thereafter, a program or application dedicated to a body fluid analysis test of the user terminal 10 may be executed to observe and image the target body fluid accommodated in the observation sheet 300 through the camera 11, thereby performing the body fluid analysis test process.

In this manner, the test device 1 for a body fluid analysis may be simply carried around by the user and collect only a target body fluid and apply the collected target body fluid to the test device, and thus the user may directly perform the body fluid test, and since the user may immediately check a result of analyzing the body fluid through the user terminal, user convenience may be improved and an accurate test result may be provided to the user.

The embodiments of the present disclosure have been described in detail, but the scope of the present disclosure is not limited thereto and various variants and modifications by a person skilled in the art using a basic concept of the present disclosure defined in claims also belong to the scope of the present disclosure.

The invention claimed is:

1. A test device for a body fluid analysis, the test device comprising:
 a first assembly having a magnifying lens for magnifying and observing a target body fluid;
 a second assembly configured to be coupled to the first assembly and having a lens transmission hole for concentrating light; and
 an observation sheet for receiving the target body fluid between the first assembly and the second assembly,
 wherein the observation sheet includes a main part disposed inside the first assembly and the second assembly and a handle part extending from the main part,
 wherein the main part includes:
 a body fluid input part configured to receive the target body fluid, comprising a pair of body fluid guide recesses formed symmetrically to direct a flow of the target body fluid into a central area of the main part and
 a body fluid guide part positioned at a height greater than the bottom of the body fluid input part, configured to guide the target body fluid received from the input part such that the fluid permeates and distributes into an inner side center of the main part.

2. The test device of claim 1, wherein the first assembly further comprises a first assembly body, a seating recess formed on an inner side of the first assembly body allowing the observation sheet to be seated therein, a through hole formed in the seating recess and penetrating the first assembly body, and at least one coupling recess formed on an upper surface of the first assembly body so as to be assembled with the second assembly.

3. The test device of claim 2, wherein the handle part may be disposed in an outer space of the first assembly and the second assembly.

4. The test device of claim 3, wherein the first assembly further comprises a first communication hole connecting the seating recess and the external space.

5. The test device of claim 4, wherein the first assembly further comprises a first circumferential step formed along an outer edge of the first assembly body to guide assembly according to coupling with the second assembly.

6. The test device of claim 5, wherein the second assembly further comprises a second assembly body and at least one coupling protrusion formed on a lower surface of the second assembly body so as to be coupled with the at least one coupling recess.

7. The test device of claim 6, wherein the second assembly further comprises a second communication hole formed in the second assembly body so that the handle part of the observation sheet is disposed in an external space.

8. The test device of claim 7, wherein the second assembly further comprises a second circumferential protrusion formed to be stepped along an outer edge of the second assembly body to guide assembly according to coupling with the first assembly.

9. The test device of claim 6, wherein the lens transmission hole penetrates from an upper side to a lower side of the second assembly body.

10. The test device of claim 2, wherein the magnifying lens is installed in the seating recess.

11. The test device of claim 1, wherein the body fluid input part comprises at least one body fluid guide recess formed in the body part to guide injection of the target body fluid.

12. The test device of claim 1, wherein the first assembly is detachably attached to a camera of a user terminal.

\* \* \* \* \*